United States Patent [19]

Amon et al.

[11] Patent Number: 5,718,726
[45] Date of Patent: Feb. 17, 1998

[54] METHOD OF ATTACHING HEPARIN TO, AND IMMOBILIZING IT ON, INORGANIC SUBSTRATE SURFACES OF CARDIOVASCULAR IMPLANTS

[75] Inventors: Michael Amon, Cadolzburg; Armin Bolz, Erlangen; Dirk Müssig, Nürnberg, all of Germany

[73] Assignee: Biotronik Mess- und Therapiegeräte GmbH & Co, Berlin, Germany

[21] Appl. No.: 712,471

[22] Filed: Sep. 11, 1996

[30] Foreign Application Priority Data

Sep. 12, 1995 [DE] Germany ............... 195 33 682.8

[51] Int. Cl.⁶ .................... A61F 2/02; A61F 2/24
[52] U.S. Cl. ........................... 623/2; 623/11
[58] Field of Search ............... 623/1, 2, 11, 12

[56] References Cited

U.S. PATENT DOCUMENTS

| 3,639,141 | 2/1972 | Dyck ............ 117/47 A |
| 4,923,465 | 5/1990 | Knoch et al. . |
| 5,002,582 | 3/1991 | Guire et al. . |
| 5,182,317 | 1/1993 | Winters et al. . |

FOREIGN PATENT DOCUMENTS

| 0528039A1 | 11/1991 | European Pat. Off. . |
| 2831360C2 | 2/1979 | Germany . |
| 4336209A1 | 3/1995 | Germany . |

*Primary Examiner*—John G. Weiss
*Assistant Examiner*—John M. Black
*Attorney, Agent, or Firm*—Browdy and Neimark

[57] ABSTRACT

A method of attaching heparin to, and immobilizing it on, inorganic substrate surfaces of cardiovascular implants such as cardiac valves or alloplastic vessel wall supports, comprising the following steps:

activation of the inorganic substrate surface by etching, attachment, by exposure to ultraviolet light, of a photoactive benzophenone compound with an amino protective group as a spacer to the activated substrate surface, splitting off of the amino protective group by the aid of a non-aqueous piperidine solution, and covalent peptide-bonding of heparin to the free and reactive amino groups of the substrate surface by an aqueous heparin solution acting on the amino groups.

10 Claims, No Drawings

METHOD OF ATTACHING HEPARIN TO, AND IMMOBILIZING IT ON, INORGANIC SUBSTRATE SURFACES OF CARDIOVASCULAR IMPLANTS

BACKGROUND OF THE INVENTION

1. Field of the Invention

The invention relates to a method of attaching heparin to, and immobilizing it on, inorganic substrate surfaces of cardiovascular implants such as cardiac valve implants or alloplastic vessel wall supports usually denoted as "stents" in technical jargon.

2. Background Art

As regards the background of the invention, it has to be explained that inserting cardiovascular implants is generally accompanied with the problem of acute thrombus formation on the surface of these implants, the blood contacting the latter tending to coagulation. So as to reduce the risk of acute thrombus formation, high doses of anti-coagulants, for example heparin preparations, are usually administered to a patient for instance by injection into the blood circulation. However, this kind of therapy involves undesired side effects and is fundamentally problematic.

An approach to solving these problems consists in chemically bonding anticoagulant drugs on the surface of the implants. As a result, for instance the heparin preparation, which catalytically prevents or at least reduces coagulation of the blood, will be employed only where these anticoagulant properties are needed, i.e. where the implant contacts the blood.

Technical methods of coating organic matters with anti-coagulants are known (see for example B. Seifert et al, "Heparinisierte Polylaktide als bioresorbierbare hämokompatible Biomaterialien", in Biomedizinische Technik 1994; 39: pages 103 to 104). Specifically in connection with chest draining catheters of polyvinyl chloride, it is known to bond a photoactive polyacrylamide-heparin (-photo-PA/HEP-) complex to the PVC material. This photo-PA/HEP coating leads to a catheter with a wettable surface and improved blood contact properties. Remnants of heparin are set free, the latter being simultaneously and covalently bonded to the surface of the catheter. With a chest draining catheter thus equipped, blood clotting and thrombus forming is minimized in the area where the catheter is in contact with the blood that accumulates in the thorax. This knowledge becomes apparent from the technical contribution to the "Surfaces in Biomaterials Symposium" of P. Gingras et al, "Surface Modification of Poly(vinyl Chloride) Chest Drainage Catheters with Anticoagulants for passive Drug Release".

SUMMARY OF THE INVENTION

Since the cardiovascular implants mentioned at the outset consist of inorganic materials such as tantalum, a titanium alloy, medical steel or pyrolytic carbon, or have an inorganic coating for instance of amorphous silicon carbide, the problem resides in finding a corresponding method to bond heparin preparations to the mentioned inorganic materials for cardiovascular implants to be able to exhibit anticoagulant properties.

The invention gives the solution of this problem. The method proposed comprises the following steps:

activation of the inorganic substrate surface by etching, attachment, by exposure to ultraviolet light, of a photoactive benzophenone compound with an amino protective group as a spacer to the activated substrate surface, splitting off of the amino protective group by the aid of a non-aqueous piperidine solution, and covalent peptide-bonding of heparin to the free and reactive amino groups of the substrate surface by an aqueous heparin solution acting on the amino groups.

In this way a cardiovascular implant can be produced having an inorganic surface to which is attached biologically active heparin with a surface concentration of typically 50 mIU/cm$^2$. Because of the covalent peptide-bonding of the heparin, the latter's activity in vitro remains unmodified for days and weeks. The heparin activity positively inhibits blood clotting on the cardiovascular implants, which can be verified by reaction times and coagulation times in thrombelastography that are prolonged by the factor 3.5 to 4 as opposed to untreated samples.

Preferred embodiments refer to advantageous developments of the method characterized above. For example, the heparin can be deposited directly on an activated substrate surface on a metal or carbon base, but also on the activated substrate surface of an amorphous silicon carbide coating of the implant. Of late, such amorphous silicon carbide coatings have experienced increased attention as a physiologically advantageous kind of coating, the positive properties of which can still be strongly improved by the attachment and immobilization of heparin, herein claimed, with a view to the use according to the invention.

In particular in connection with an amorphous silicon carbide coating, the activation of the substrate surface preferably effected by etching by means of aqueous hydrofluoric acid leads to effective protonation of the surface, supporting the efficiency of the further attachment mechanism.

The Fmoc-p-Bz-Phe—OH solution in N,N'-dimethyl formamide (DMF) preferably used as the photoactive benzophenone compound is based on a commercial product Fmoc-pBz-Phe—OH, which of course simplifies the manufacturing process and renders it more rational.

The invention further relates to preferred method parameters in connection with the aqueous heparin solution used. Further information about this will become apparent from the description of the exemplary embodiment.

A cardiovascular implant can be produced with the aid of the method according to the invention so that heparin is attached to, and mobilized on, the substrate surface as an anticoagulant by means of a covalent peptide bond. Preferably, the substrate surface if formed by a coating of amorphous silicon carbide.

Further features, details and advantages of the invention will become apparent from the ensuing exemplary embodiment.

DESCRIPTION OF THE PREFERRED EMBODIMENT

To begin with, the method according to the invention is described on the basis of the attachment of heparin to, and its immobilization on, a silicon carbide (a-SiC:H) coating (sample surface of tantalum with a coating of amorphous silicon carbide, sample size 5×10×1 mm$^3$). However, the corresponding process and the results obtained from the sample, as they will still be explained in detail below, can easily be conferred to the attachment of heparin to, and its immobilization on, stents which are provided with a silicon carbide coating.

The process can be specified as follows: The silicon carbide surface is etched by the aid of a 40 per cent aqueous hydrofluoric acid. This etching leads to the attachment of protons to the surface, which can be determined by conventional infrared spectroscopic examination of the a-SiC:H surface.

Then the sample surface is rinsed with water, incubation of the sample taking place in 2 ml of a $20\times10^{-6}$ molar Fmoc-p-Bz-Phe—OH solution in N,N' dimethyl formamide (DMF). The Fmoc-p-Bz-Phe—OH solution acting as a photoactive spacer substance can be bought as the commercial product "Fmoc-p-Bz-Phe—OH", product number B 2220, of the company of "Bachem Biochemica GmbH" of Heidelberg. The reduction of benzophenone is initiated by exposure to ultraviolet light. After exposure to ultra-violet light, the reaction solution is poured off and the sample is rinsed several times with distilled water.

The next step resides in splitting off the Fmoc protective group by means of a 25 per cent piperidine solution in DMF. The bonding of the heparin is effected to the amino group now set free and reactive. To this end, the sample is incubated in 1 ml of an aqueous solution consisting of 10,000 IU heparin and 50 mg N-(3-dimethylaminopropyl)-N'-ethylcarbodiimide-hydrochloride for some hours e.g. 2 to 6 hours at ambient temperature. This reaction is terminated by fritting the reaction solution.

The process specified above serves to build up a silicon-carbide-spacer-heparin complex on the silicon carbide surface, corresponding to the following structural formula.

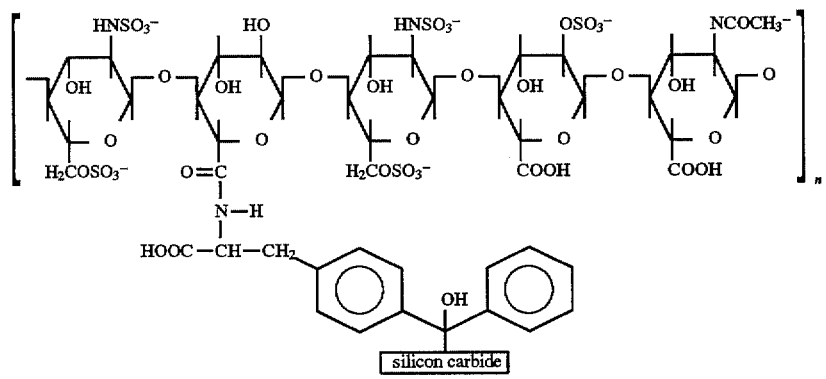

By means of relevant biochemical methods, the surface concentration of the biologically active heparin on the sample can be determined to amount to 50 mIU/cm². Samples of this kind were subjected to another intensive process of rising in a physiological salt solution so as to simulate the behavior of the heparin coating in the blood stream. Corresponding tests have shown at the biological activity does not decrease even after two weeks of rinsing. This means that virtually a 100 per cent immobilization of the heparin takes place on the silicon carbide surface.

Further, the influence of the heparin-added coating on blood coagulation was determined by the comparison of the thrombelastograms of samples having a silicon carbide coating with and without heparin attachment. The thrombelastography famished reaction times and coagulation times which, in the case of samples with heparin attachment, exceeded those of silicon carbide coated samples without heparin attachment by the factor 3.5 or 4, respectively. This retardation of blood coagulation shows that, owing to its biological activity, the silicon carbide coating with heparin attachment inhibits blood coagulation on cardiovascular implants.

What is claimed is:

1. A method of attaching heparin to, and mobilizing the heparin on, inorganic substrate surfaces of cardiovascular implants such as cardiac valves or alloplastic vessel wall supports, comprising the following steps:
   activation of the inorganic substrate surface by etching,
   attachment, by exposure to ultraviolet light, of a photoactive benzophenone compound with an amino protective group as a spacer to the activated substrate surface,
   splitting off of the amino protective group by the aid of a non-aqueous piperidine solution, and
   covalent peptide-bonding of heparin to the free and reactive amino groups of the substrate surface by an aqueous heparin solution acting on the amino groups.

2. A method according to claim 1, wherein heparin is attached to an activated substrate surface of tantalium, a titanium alloy, medical steel or pyrolytic carbon, where the heparin is immobilized.

3. A method according to claim 1, wherein heparin is attached to the activated substrate surface of an amorphous silicon carbide coating of the implant, where the heparin is mobilized.

4. A method according to claim 1, wherein the activation of the substrate surface takes place by etching by means of aqueous hydrofluoric acid.

5. A method according to claim 1, wherein a Fmoc-p-Bz-Phe—OH solution in N,N'-dimethyl formamide is used as the photoactive benzophenone compound.

6. A method according to claim 1, wherein the acqueous heparin solution consists of heparin with N-(3-dimethylaminopropyl)-N'-ethylcarbodiimide-hydrochloride in water.

7. A method according to claim 6, wherein 1 ml of the aqueous heparin solution, contains 10,000 IU heparin and 50 mg N-(3-dimethylaminopropyl)-N'-ethylcarbodiimide-hydrochloride.

8. A method according to claim 6, wherein the aqueous heparin solution acts on the substrate surface for a period of 2 to 6 hours at ambient temperature.

9. A cardiovascular implant, such as an artificial cardiac valve or alloplastic vessel wall support, produced in accordance with a method according to claim 1 and having an inorganic substrate surface, wherein heparin is attached to, and immobilized on, the substrate surface by means of a covalent peptide bond.

10. A cardiovascular implant according to claim 9, wherein the substrate surface is formed by a coating of amorphous silicon carbide.

* * * * *